United States Patent [19]

Lasker

[11] Patent Number: 5,571,521
[45] Date of Patent: Nov. 5, 1996

[54] COMPOSITION CONTAINING SILVER AMMONIUM PHENYTOIN COMPLEX AND A PHENYTOIN AND USE OF SAID COMPOSITION

[76] Inventor: Sigmund E. Lasker, New York Medical College, Valhalla, N.Y. 10595

[21] Appl. No.: 387,251

[22] Filed: Feb. 13, 1995

Related U.S. Application Data

[63] Continuation-in-part of Ser. No. 178,768, Jan. 7, 1994, Pat. No. 5,439,903, which is a continuation of Ser. No. 974,686, Nov. 12, 1992, Pat. No. 5,298,264, which is a continuation of Ser. No. 765,460, Sep. 25, 1991, abandoned, which is a continuation of Ser. No. 363,288, Jun. 2, 1989, abandoned, which is a continuation of Ser. No. 862,160, May 12, 1986, abandoned, which is a continuation of Ser. No. 570,800, Jan. 16, 1984, abandoned.

[51] Int. Cl.$^6$ .............................. A61K 9/06; A61K 9/14; A61L 15/00
[52] U.S. Cl. ..................... 424/409; 424/405; 424/408; 514/969
[58] Field of Search ................... 424/443, 408, 424/445, 409, 449; 514/184, 969; 548/107

[56] References Cited

U.S. PATENT DOCUMENTS 5,298,624  3/1994  Lasker ........................ 548/107

*Primary Examiner*—Thurman K. Page
*Assistant Examiner*—Sharon Howard
*Attorney, Agent, or Firm*—Cooper & Dunham

[57] ABSTRACT

Compositions containing silver ammonium phenytoin complex and a phenytoin are usefully employed, particularly when applied topically, for the treatment of animal or human tissue, for wound healing and are useful in wound dressing preparations for the prevention or treatment of infections. The compositions are usefully applied by direct topical application to the wound or tissue to be treated or may be directly applied to the wound or tissue or incorporated in or coated on a dressing, such as a bandage.

33 Claims, No Drawings

COMPOSITION CONTAINING SILVER AMMONIUM PHENYTOIN COMPLEX AND A PHENYTOIN AND USE OF SAID COMPOSITION

This application is a continuation in part of patent application Ser. No. 178,768 filed Jan. 7, 1994, now U.S. Pat. No. 5,439,903, which, in turn, is a continuation of patent application Ser. No. 974,686 filed Nov. 12, 1992, now U.S. Pat. No. 5,298,264, which in turn is a continuation of patent application Ser. No. 765,460 filed Sep. 25, 1991 (abandoned) which, in turn, is a continuation of patent application Ser. No. 363,288 filed Jun. 2, 1989 (abandoned) which, in turn, is a continuation of patent application Ser. No. 862,160 filed May 12, 1986 (abandoned) which, in turn, is a continuation of patent application Ser. No. 570,800 filed Jan. 16, 1984 (abandoned).

BACKGROUND OF THE INVENTION

The compound 5,5-diphenyl-2,4 imidazolidinedione, also known as diphenyl hydantoin, or phenytoin possesses the structure

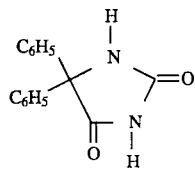

and is used as an anticonvulsant. It is also used in animal husbandry as an anticonvulsant, particularly in the treatment of cats.

Phenytoin, its derivatives, and compositions containing the same are well known in the art, see U.S. Pat. Nos. 2,409,754; 3,932,449; 3,798,233; 4,093,809, the disclosures of which are incorporated herein. While many uses for phenytoin and its derivatives are disclosed in these patents, it is apparent that phenytoin and its derivatives have not been employed as biocides.

Organometallic compounds have been employed as specific biocides, particularly as antimicrobials. For example, organometallic derivatives of sulfadiazine are among the most prominent of these materials. see U.S. Pat. Nos. 3,761,590; 4,020,150; 4,049,802; 3,792,161; and 4,078,058, in which organometallic compounds of sulfadiazine are disclosed, such as silver sulfadiazine, zinc sulfadiazine, and cerium sulfadiazine. While each of these compounds exhibits satisfactory effect in particular applications, no single one of these compounds, or class of these compounds, is effective against a broad range of infections and infective agents such as bacteria, viruses, plasmodia, and the like. Additionally, treatment of certain microbial infections with metallic compounds or complexes of sulfadiazine has resulted in the development of resistant microbial strains.

Hence, it is an object of this invention to provide compositions useful as a versatile biocide for the treatment of infections, such as infections caused by bacteria, viruses and plasmodia.

It is another object of this invention to provide compositions useful for wound treatment.

It is a further object of this invention to provide compositions and methods of employing same for treating and/or preventing infections in plant and animal tissue by direct topical application thereto of such compositions.

SUMMARY OF THE INVENTION

The compound 5,5-diphenyl-2,4 imidazolidinedione or phenytoin, particularly its salts, especially its ammonium salt or derivative, is reacted with a compound containing metallic ions under conditions favorable to production of complexes of the form Me(Ph), where Me stands for a metal ion, which may be chosen from, e.g. Ag, Zn, Cu, Ce, Fe, and Hg and the like, and Ph stands for a phenytoin. The resulting organometallic compounds or complexes, particularly the ammonium complex when combined or employed with phenytoin are useful as biocides in the treatment of various plant, human and animal infections, such as bacterial infections, viral infections, fungal infections, parasite infections, and plant infestations by insects or other pests, and also improve the healing of wounds and injured tissue, particularly infected tissue and wounds. Infected wounds, such as infected diabetic ulcers and infected decubitus ulcers, are effectively treated for healing by the compositions of this invention.

The compositions of this invention demonstrate bimodal activity, antibacterial and growth promoting and healing properties. To maximize these properties or activities in vivo with greatest effectiveness, particularly for infected wounds, the compositions of this invention, when employed for the treatment of infected wound, and also non-infected wounds, would comprise the highest proportion or concentration of a phenytoin free acid effective for wound healing and the minimal effective proportion or amount or concentration of silver phenytoin ammonium complex for antibacterial activity. In this connection, for the minimal inhibiting concentrations of various antibacterial agents, including silver ammonium diphenyl hydantoin or silver phenytoin ammonium complex, see the values or concentrations listed in accompanying Table 2.

compositions containing the phenytoin-containing organometallic complexes and phenytoin are applied, either topically or parenterally, to plant and/or animal tissue so as to prevent or to treat or promote healing of infections and injuries. Additionally, the organometallic complexes may be combined with other materials which are designed to prevent infestation or infection, or to relieve infection and/or promote healing.

The fact that low toxicity toward host tissue is observed, particularly in the case of the silver ammonium phenytoin complex, renders the silver ammonium phenytoin complex and phenytoin-containing compositions especially suitable for use as a topical agent in burn therapy or in the treatment of the umbilical stump of newborn infants. Accordingly, the silver ammonium phenytoin and phenytoin-containing compositions of this invention are particularly useful.

DETAILED DESCRIPTION OF THE INVENTION

Phenytoin is converted to its ammonium salt by reacting it with ammonium hydroxide under conditions favoring formation of the ammonium salt. Following formation of the ammonium salt, a source of the metal ion with which the phenytoin is to be complexed is added. A suitable such source is an aqueous silver nitrate when the desired product to be produced is silver ammonium phenytoin. However, any appropriate compound which provides the metallic ion to be complexed may be employed. Some of the metallic ions which may be complexed are the ions of Ag, Zn, Cu, Ce, Fe and Hg and others. The source of metallic ions is added under conditions favoring formation of the respective organometallic-phenytoin or diphenyl hydantoin complex. The resulting complexes are, in general, poorly soluble. The formation of a precipitate is an indication that the complex has formed. Silver ammonium phenytoin is very insoluble and precipitates out of the reaction solution almost immediately. Upon precipitation, the metal ammonium phenytoin is collected, washed free of reactants and then dried and readied for use.

The following examples demonstrate uses of the silver ammonium phenytoin complex in compositions of this invention. The fact that silver ammonium phenytoin alone is used should not be understood to limit the scope of this invention.

The poor solubility of silver ammonium phenytoin in aqueous media in some instances requires special techniques to achieve the desired results.

EXAMPLE I

The effect of silver ammonium phenytoin at various concentrations upon various microorganisms was tested. For each of the microorganisms listed below a culture was grown in Miller-Hinton broth (24 hour culture), and then diluted at a 1:100 ratio. This diluted culture was then grown for an additional two hours, after which the silver diphenyl hydantoin was added. Evaluation of the culture took place 18 hours after the addition of the silver ammonium phenytoin. The results are summarized in accompanying Table 1:

TABLE 1

Effect of Silver Ammonium Phenytoin on Various Microorganisms Minimal Inhibitory Concentration Micrograms of Silver Ammonium Diphenyl Hydantoin per Millilter

| Organism | 1 | 10 | 20 | 40 |
|---|---|---|---|---|
| Enterococcus Group D Strep | – | – | + | ++ |

TABLE 1-continued

Effect of Silver Ammonium Phenytoin on Various Microorganisms Minimal Inhibitory Concentration Micrograms of Silver Ammonium Diphenyl Hydantoin per Millilter

| Organism | 1 | 10 | 20 | 40 |
|---|---|---|---|---|
| Candida Albicans | – | – | + | + |
| Klebsiella | + | + | + | ++ |
| Seratia | – | + | + | + |
| Pseudomonas aeruginosa | – | – | + | + |
| Staphloccoccus aereus | – | – | + | + |

+ = inhibition
Organisms grown in Miller-Hinton broth
A 24 hour culture was diluted 1:100 and compound was added to a two hour culture of this dilution and evaluated at 18 hours.
Antibacterial action, was also demonstrated in pure cultures of organisms on blood agar plates.

EXAMPLE II

Experiments designed to compare the effect of sodium sulfadiazine, silver sutfadiazine, and silver ammonium phenytoin were performed. The parameters of the experiments were identical to those set forth in Example I, and the results are set forth in Table 2.

TABLE 2

MINIMAL INHIBITORY CONCENTRATIONS

| | Enterococcus | | | Candida A. | | | Klebsiella | | | Serratia M. | | | Pseudomonas A. | | | Strep. A | | |
|---|---|---|---|---|---|---|---|---|---|---|---|---|---|---|---|---|---|---|
| | S | SS | SP | S | SS | SP | S | SS | SP | S | SS | SP | S | SS | SP | S | SS | SP |
| Microgram of agent | | | | | | | | | | | | | | | | | | |
| 1 | – | – | – | – | – | – | – | – | + | – | – | – | – | – | – | – | – | – |
| 10 | – | – | – | – | – | – | – | – | + | – | + | + | – | + | – | – | – | – |
| 20 | – | – | + | – | – | + | – | + | + | ± | + | + | – | + | + | – | + | + |
| 40 | – | + | ++ | – | – | + | – | + | ++ | ± | + | ++ | – | + | + | + | + | + |

Organisms were grown in Miller-Hinton broth. A twenty-four hour culture was diluted 1:100. Compounds were added to two hour cultures and examined for inhibition at 18 hours. The magnitude of inhibition is estimated and indicated by +.
S. Sodium Sulfadimene
SS: Silver Sulfadiazine
SP: Silver Ammonium Diphenyl Hydantoin

EXAMPLE 3

The efficacy of silver ammonium phenytoin as a plant fungicide was tested. Silver ammonium phenytoin and the selected commercial fungicide were ground and suspended in acetone in an amount equal to 6% of their final volume and then suspended in purified water containing 250 ppm of the surfactant TREM 014 (polyhydric alcohol esters).

In the tests, the results of which are summarized in Tables 3–6, the suspensions were sprayed to the point of run-off on the plants which were then inoculated 24 hours with a spore suspension of the fungus as given in Tables 3–6. The thus treated plants were then placed in a saturated humidity chamber at 20° C. for 24 hour, and then in a growth chamber for an additional 7–12 days. Disease ratings were then made, and recorded as percent disease control.

Curative tests were conducted in a similar matter, except that inoculation with spore fungus took place 24 hours prior to application. The results are summarized in Tables 3–6.

TABLE 3

Evaluation of silver ammonium phenytoin for the control of grape downy mildew (*Plasmopara viticola*)[1]

| Compound | Concentration[2] | Percent Disease Control | |
|---|---|---|---|
| | | Preventive[3] | Curative[4] |
| Silver | 100 | 87 | 0 |
| ammonium | 20 | 49 | 0 |
| phenytoin | 5 | 24 | 0 |
| Curzate ® | 100 | 100 | 100 |
| | 20 | 0 | 100 |
| | 5 | 0 | 0 |
| Manzate ® | 100 | 100 | 0 |
| | 20 | 80 | —[5] |
| | 5 | 40 | — |

[1]Test plants inoculated with an aqueous sporangial suspension (1.0 × 10$^5$ sporangia/ml.)
[2]ppm
[3]Test plants inoculated 24 hours after application of chemical
[4]Test plants inoculated 24 hours before application of chemical
[5]not tested
Note:
Curzate ® is the registered trademark of E. I. du Pont de Nemours & Co. for formulation of 2-cyano-N-(ethyl-amino) carbonyl-2-methoxyamino) acetamide
Manzate ® is the registered trademark of E. I. du Pont de Nemours & Co. for formulations of Manganese ethylenebisdithio carbamate

TABLE 4

Evaluation of silver ammonium phenytoin for the control of tomato late blight (*Phytophthora infestans*)[1]

| Compound | Concentration[2] | Percent Disease Control |
|---|---|---|
| Silver | 100 | 98 |
| ammonium | 20 | 95 |
| phenytoin | 5 | 17 |
| Curzate ® | 100 | 100 |
| | 20 | 90 |
| | 5 | 40 |
| Manzate ® | 100 | 100 |
| | 20 | 90 |
| | 5 | 0 |

[1]Test plants inoculated with aqueous sporangial suspension (2.0 × 10$^4$) sporangia/ml).
[2]ppm

TABLE 5

Evaluation of silver ammonium phenytoin for the control of apple scab (*Venturia inaequalis*)[1]

| Compound | Concentration[2] | Percent Disease Control | |
|---|---|---|---|
| | | Preventive[3] | Curative[4] |
| Silver | 100 | 98 | |
| ammonium | 20 | 95 | |
| phenytoin | 5 | 17 | |
| Curzate ® | 100 | 100 | |
| | 20 | 90 | |

TABLE 5-continued

Evaluation of silver ammonium phenytoin for the control of apple scab (*Venturia inaequalis*)[1]

| Compound | Concentration[2] | Percent Disease Control | |
|---|---|---|---|
| | | Preventive[3] | Curative[4] |
| | 5 | 40 | |
| Manzate ® | 100 | 100 | |
| | 20 | 90 | |
| | 5 | 0 | |

[1]Test plants inoculated with aqueous conidial suspension (1.5 × 10$^4$ condida/ml.
[2]ppm
[3]Test plants inoculated 24 hours after application of chemical
[4]Test plants inoculated 24 hours before application of chemical
Baycor ® is the registered trademark of Bayer AG (Federal Republic of Germany) and Mobay Chemical Corp. Agricultural Chemicals Division, for formulations of B (1,1-Biphenyl)-4-ylox)a (1,1 dimethylethyl)-1H-1,2,4 trizaole-ethanol

TABLE 6

Evaluation of silver ammonium phenytoin for the control of peanut leafspot (*Cercospora arachidicola*)[1]

| Compound | Concentration[2] | Percent Disease Control | |
|---|---|---|---|
| | | Preventive[3] | Curative[4] |
| Silver | 100 | 78 | 60 |
| ammonium | 20 | — | 0 |
| phenytoin | 5 | 16 | 0 |
| Manzate ® | 100 | 85 | 0 |
| | 20 | 30 | 0 |
| | 5 | 0 | 0 |
| Baycor ® | 20 | 100 | 100 |
| | 5 | 98 | 100 |
| | 1 | 77 | 92 |

[1]Test plants inoculated with aqueous conidial suspension (6.0 × 10$^4$ conidia/ml).
[2]ppm.
[3]Test plants inoculated 24 hours after application of chemical
[4]Test plants inoculated 24 hours before application of chemical Silver ammonium complexes, particularly silver ammonium phenytoin, are effective against various infectious agents, including bacteria, viruses, fungi, parasites, and insects. It has been found, in particular, that silver ammonium phenytoin combination with a phenytoin, particularly the compound phenytoin or its salt, such as its sodium salt, is useful against parasitic infections, including, but not limited to, all species of malaria-carrying plasmodia sporozoa.

Additionally, it is found that phenytoin compounds accumulate in tumor cells. Hence, the compositions may be used in the delivery of the complexing metal, e.g. Ag, to tumor cells. The accumulated organometallic ammonium phenytoin complex allows diffusion of the metal ion to the tumor cells resulting in a gradual release of the complex compounds.

The method of delivery of the organometallic compositions containing the phenytoin and silver ammonium complex will vary depending upon the type and extent of the infection or wound being treated. Topical application is particularly desirable when the tissue or wound is open or presents a surface which is already susceptible of infection, such as a burn wound. This topical method of application is particularly appropriate in treating other animal or human tissues, such as plant tissue infections.

Application of the composition of this invention may be accomplished parenterally as well as subcutaneous injection, intravenous application, intramuscular injection and the like. Parenteral application is particularly well suited for treating animal tissue infections, such as blood or muscle tissue infections. It is also the preferred method of application when a gradual release or the organometallic complex is desired, such as in the treatment of tumor cells.

Some embodiments of the metallo ammonium phenytoin complexes which are suitable for topical or parenteral application are creams or ointments, wherein one or more inert ingredients are combined with the complex to aid in its delivery to plant and animal tissue. Liquid carriers may be used, such as in aqueous dispersions, intravenous fluids, aerosols and sprays. Additionally materials which may be used as sources for the organometallic complexes include dusts, dusting powders, and tinctures of the compounds or compositions containing the compounds.

Other media may be used for large scale protection from infection or infestation. While suspensions of organometallic complexes may be used to spray plants, other media, such as plant stakes treated with the compound, or protective covers, and the like may be employed. Similarly, the compounds may be incorporated with or impregnated in dressings, such as bandages, mosquito netting or other protective coverings. Cements, paints, coatings and other materials for the treatment of plants and trees may have incorporated therein or be impregnated with the compositions of this invention. Such paints, coatings and cements will act to render dwellings, shelters, etc. more infection and infestation, e.g. insect infestation, proof than previously possible.

As will be apparent to those skilled in the art, many modifications, alterations, and substitutions are possible, in light of the foregoing disclosures, without departing from the spirit of this invention.

What is claimed is:

1. A composition comprising silver phenytoin and a phenytoin.
2. A composition in accordance with claim 1 wherein said silver phenytoin is silver ammonium phenytoin.
3. A composition in accordance with claim 1 wherein said phenytoin is the compound phenytoin.
4. A composition in accordance with claim 1 wherein said silver phenytoin is present in an amount in the range 1–99% by weight of said composition.
5. A composition in accordance with claim 1 wherein said phenytoin is present in an amount in the range 1–99% by weight of said composition.
6. A composition in accordance with claim 1 wherein said phenytoin is sodium phenytoin.
7. A composition in accordance with claim 2 wherein the combined amounts of said silver ammonium phenytoin complex and said phenytoin in said composition is in the range 0.1–100% by weight of said composition.
8. A composition in accordance with claim 7 wherein said silver phenytoin ammonium complex and said phenytoin are present in said composition in the amounts relative to each other in the range 1–99 parts by weight silver ammonium phenytoin complex and 99–1 parts by weight phenytoin.
9. A composition in accordance with claim 1 consisting essentially of silver ammonium phenytoin complex and a phenytoin.
10. A composition in accordance with claim 9 wherein said phenytoin is the compound phenytoin.
11. A composition in accordance with claim 9 wherein said phenytoin is a phenytoin salt.
12. A composition in accordance with claim 9 wherein said phenytoin salt is sodium phenytoin.
13. A composition in accordance with claim 1 comprising silver ammonium phenytoin complex and said phenytoin and a fluid, liquid or gaseous carrier.
14. A composition in accordance with claim 1 comprising said silver ammonium phenytoin complex and said phenytoin and a finely divided particulate solids carrier.
15. A composition in accordance with claim 1 comprising said silver ammonium phenytoin complex, said phenytoin and a fibrous carrier.
16. A composition in accordance with claim 15 wherein said fibrous carrier is a bandage wherein said silver ammonium phenytoin complex and said phenytoin are coated onto or impregnated into or dispersed within said carrier.
17. A method of treating a wound or tissue for healing which comprises the administration thereto of a composition in accordance with claim 1.
18. A method for treating a wound or tissue for healing which comprises the administration thereto of a composition in accordance with claim 2.
19. A method for treating a wound or tissue for healing which comprises the administration thereto of a composition in accordance with claim 3.
20. A method for treating a wound or tissue for healing which comprises the administration thereto of a composition in accordance with claim 4.
21. A method for treating a wound or tissue for healing which comprises the administration thereto of a composition in accordance with claim 5.
22. A method of treating a wound or tissue for healing which comprises the administration thereto of a composition in accordance with claim 6.
23. A method of treating a wound or tissue for healing which comprises the administration thereto of a composition in accordance with claim 7.
24. A wound or tissue dressing for application to a wound or tissue for healing comprising silver ammonium phenytoin complex and a phenytoin.
25. A wound or tissue dressing in accordance with claim 24 wherein said dressing is an ointment.
26. A wound or tissue dressing in accordance with claim 24 wherein said dressing comprises a bandage containing or impregnated with silver ammonium phenytoin complex and phenytoin.
27. A method of treating wound or tissue for healing which comprises topically applying to said wound or tissue a composition comprising silver ammonium phenytoin complex and a phenytoin.
28. A method in accordance with claim 27 wherein said phenytoin is the compound phenytoin.
29. A method in accordance with claim 27 wherein said phenytoin is a salt of the compound phenytoin.
30. A method in accordance with claim 27 wherein said phenytoin is the compound sodium phenytoin.
31. A method in accordance with claim 27 wherein said composition is topically applied directly onto said wound or tissue.
32. A method in accordance with claim 27 wherein said composition comprises silver ammonium phenytoin and a phenytoin in finely divided particulate form and is applied directly onto said wound or tissue.
33. A method in accordance with claim 27 wherein said composition comprises silver ammonium phenytoin complex and a phenytoin in dry, finely divided form and the composition is applied topically directly onto said wound or tissue.

* * * * *